United States Patent [19]

Onopchenko et al.

[11] Patent Number: 4,572,791
[45] Date of Patent: Feb. 25, 1986

[54] PRODUCTION OF SATURATED AND UNSATURATED SILAHYDROCARBON MIXTURES USING RHODIUM CATALYST, AND TO PRODUCTS PRODUCED THEREBY

[75] Inventors: Anatoli Onopchenko, Monroeville; Edward T. Sabourin, Allison Park, both of Pa.

[73] Assignee: Gulf Research & Development Company, Pittsburgh, Pa.

[21] Appl. No.: 678,792

[22] Filed: Dec. 6, 1984

[51] Int. Cl.$^4$ .................. C10M 1/14; C10M 1/54
[52] U.S. Cl. .................. 252/46.3; 252/49.6; 556/429; 556/465
[58] Field of Search .......... 556/465, 481, 479, 429; 252/46.3, 49.6

[56] References Cited

U.S. PATENT DOCUMENTS

| | | | |
|---|---|---|---|
| 2,721,873 | 10/1955 | Mackenzie et al. | 556/479 |
| 2,823,218 | 2/1958 | Speier et al. | 556/479 X |
| 2,851,473 | 9/1958 | Wagner et al. | 556/479 |
| 3,159,662 | 12/1964 | Ashby | 556/479 X |
| 3,220,972 | 11/1965 | Lamoreaux | 260/46.5 |
| 3,296,291 | 1/1967 | Chalk et al. | 556/479 X |
| 3,465,017 | 9/1969 | Coutant | 252/49.6 X |
| 3,470,225 | 9/1969 | Knorre et al. | 556/479 |
| 3,546,266 | 12/1970 | Coffey | 556/479 |
| 3,798,252 | 3/1974 | Nitzsche et al. | 556/479 X |
| 3,814,730 | 6/1974 | Karstedt | 260/46.5 UA |
| 3,865,858 | 2/1975 | Ossko et al. | 556/479 X |
| 4,218,331 | 8/1980 | Bacha et al. | 252/48.6 |
| 4,222,951 | 9/1980 | Kreis et al. | 556/478 |
| 4,292,434 | 9/1981 | Lindner et al. | 556/479 |

FOREIGN PATENT DOCUMENTS

1347845  2/1974  United Kingdom .

OTHER PUBLICATIONS

Millan et al., J.C.S. Chem. Comm., pp. 673-674 (1981).
Koroleva et al., Zh. Obsch. Khim., 37 (12), 2768, 1967.
Speier, J. L., Advances in Organometallic Chemistry, vol. 17, Academic Press, pp. 407-415, 1979.
Washburne, S. S., "Silicon Compounds Register & Review," Petrarch Systems, Inc., Bristol, PA 19007, p. 10, 1982.
Green et al., J. Chem. Soc. Dalton, 1519-1522, 1977.

*Primary Examiner*—W. J. Shine
*Attorney, Agent, or Firm*—Roylance, Abrams, Berdo & Goodman

[57] ABSTRACT

The silahydrocarbon product containing at least 75 weight percent of saturated silahydrocarbons with the remainder being unsaturated silahydrocarbons is produced by a process in which admixture comprising
(A) at least one alpha-olefin containing from 2 to about 20 carbon atoms per molecule, and
(B) at least one alkylsilane selected from the group consisting of
  (i) a dialkylsilane having the formula

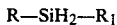

$R\text{—}SiH_2\text{—}R_1$ (ii) a trialkylsilane having the formula

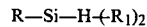

$R\text{—}Si\text{—}H\text{—}(R_1)_2$ and
  (iii) mixtures thereof, wherein R and $R_1$, the same or different, each represent an alkyl radical of from one to 20 carbon atoms per molecule with a catalyst comprising a homogeneous rhodium-containing catalyst or a heterogeneous rhodium-containing catalyst in a halogen-free inert solvent, under hydrosilylation reaction conditions to produce a mixture containing saturated and unsaturated silane hydrocarbons useful as lubricants. The unsaturated silane hydrocarbons can be substituted with sulfur to provide improved lubricating characteristics.

24 Claims, No Drawings

PRODUCTION OF SATURATED AND UNSATURATED SILAHYDROCARBON MIXTURES USING RHODIUM CATALYST, AND TO PRODUCTS PRODUCED THEREBY

FIELD OF THE INVENTION

The present invention relates to the production of mixtures of saturated and unsaturated silahydrocarbons. More particularly, this invention relates to the production of mixtures of saturated and unsaturated silahydrocarbons from dialkylsilanes, trialkylsilanes and mixtures thereof, to the unsaturated products produced by such process, to lubricating oils containing such products and to sulfur substituted silahydrocarbons.

BACKGROUND INFORMATION

Various synthetic fluids, including synthetic hydrocarbons and silahydrocarbons, have been developed which are useful in the formulation of hydraulic fluids and lubricants which are stable at high temperatures. Tetraalkylsubstituted silanes have been proposed for use in the formulation of hydraulic fluids and lubricants since they possess excellent viscosities over a wide temperature range, low pour points, and exhibit excellent thermal stabilities.

Various methods have been proposed for synthesizing tetraalkylsilanes involving the addition of a Grignard reagent or alkyllithium compounds to alkyltrichlorosilanes. Such processes are described in U.S. Pat. No. 4,367,343 to Tamborski et al; Rosenberg et al, *J. Org. Chem.*, 1960, Vol. 25, pp. 243–248; and Baum et al, *J. Chem. Eng. Data*, 1961, Vol. 6, No. 1, pp. 142–145.

Reaction of alpha-olefin with triethylsilane to form vinylsilanes and allylsilanes using rhodium complexes is described by Millan et al, *J. C. S. Chem. Comm.*, 1981, pp. 673–674. The use of a rhodium catalyst is described as producing, at best, 90 percent saturated product with the remainder being unsaturated silahydrocarbons at a total yield of 40 percent. Conditions producing higher total yields gave about 50 percent unsaturated products. The presence of unsaturation in the silahydrocarbon molecule has been considered highly undesirable when such compounds are to be used in the formulation of hydraulic fluids and lubricants. Olefinic compounds cause color formation during storage, and lead to formation of gums and sludge in engines as well as premature oxidation. Normally, such unsaturated products would have to be subjected to hydrogenation, at additional expense, to provide the corresponding saturated product.

SUMMARY OF THE INVENTION

It has now been found that a mixture of saturated and unsaturated silahydrocarbons can be produced in high yield using a rhodium-containing catalyst in which such admixture contains at least 75 percent saturated silahydrocarbon. The process of the present invention comprises contacting an admixture comprising:
(A) at least one alpha-olefin containing from 2 to about 20 carbon atoms per molecule, preferably from 8 to 20 carbon atoms per molecule, and
(B) at least one alkylsilane selected from the group consisting of
(i) a dialkylsilane having the formula $$R-SiH_2-R_1$$

(ii) a trialkylsilane having the formula $$R-SiH-(R_1)_2$$

and
(iii) mixtures thereof,
wherein R and $R_1$, the same or different, each represent an alkyl radical of from one to 20 carbon atoms per molecule.

The reaction mixture is contacted with a catalyst comprising a homogeneous rhodium-containing catalyst having a basicity substantially equal to or less than that provided by a rhodium-containing catalyst having a triphenyl phosphine ligand or a heterogeneous rhodium-containing catalyst in halogen-free inert solvent, under hydrosilylation reaction conditions. Surprisingly, it was discovered that the use such rhodium-containing catalyst in a halogen-free inert solvent provides a mixture of saturated and unsaturated silane hydrocarbons containing at least 75 percent saturated product even at complete conversion.

The unsaturated products produced in accordance with the present invention have the following formula:

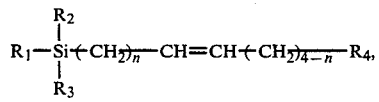

wherein $R_1$ represents an alkyl group having from one to about 20 carbon atoms per molecule, $R_2$ and $R_3$ each represent the same or different alkyl groups having from 6 to about 20 carbon atoms per molecule, $R_4$ represents an alkyl group having from one to about 8 carbon atoms per molecule, and n represents an integer from 0 to 4, inclusive with the proviso that the molecular weight of the unsaturated silane hydrocarbon is above 300.

Without limiting the present invention to any particular theory or mechanism, it is believed that the use of a halogen-free solvent in combination with the rhodium-containing catalyst of the present invention permits an increase in production of the saturated species of silahydrocarbon by rendering the yield of saturated silahydrocarbons reaction temperature dependent. While the production of saturated silahydrocarbons was thought to be substantially temperature independent, the ratio of saturated to unsaturated silahydrocarbons can be increased in accordance with the process of the present invention by increasing reaction temperature. Thus, the process of the present invention enables the control of the product mix of saturated and unsaturated silahydrocarbons to a desired ratio.

According to an embodiment of the process of the present invention, the process is conducted in the presence of a halogen-free inert solvent comprising saturated silahydrocarbon product thus eliminating the need for extraneous solvent.

According to another embodiment of the present invention, the mixture of saturated and unsaturated silanes produced in accordance with the process of the present invention is used as a component of a hydraulic fluid or lubricant. Surprisingly, it has been found that the presence of unsaturation in the silahydrocarbon product does not significantly alter the product quality if the amount of unsaturated silahydrocarbon is below about 25 weight percent with the remainder being saturated silahydrocarbon.

According to still another embodiment of the present invention, the silahydrocarbon product is reacted with a sulfur or phosphorus-containing moiety so as to substitute sulfur or phosphorus into the unsaturated silahydrocarbon product to reduce unsaturation. Such substitution not only improves stability of the product, but improves the lubricating characteristics of the silahydrocarbon product when used as a lubricating oil component.

DESCRIPTION OF THE PREFERRED EMBODIMENTS

As previously indicated, the present process involves reacting an alpha-olefin with at least one alkylsilane from the group consisting of (i) a dialkyl silane having the formula

$R-SiH_2-R_1$ (ii) a trialkylsilane having the formula

$R-SiH(R_1)_2$ or (iii) mixtures thereof, wherein R and $R_1$, the same or different, each represent an alkyl radical of from one to 20 carbon atoms per molecule.

Suitable dialkyl silanes include methyloctylsilane, methyldecylsilane, ethyloctylsilane, ethyldecylsilane, methylhexylsilane, butyloctylsilane, hexyloctylsilane, dioctylsilane, didecylsilane, hexyltetradecylsilane, hexyltetradecylsilane, octyldodecylsilane, and various mixtures.

Suitable trialkylsilanes include methyldi(octyl)silane, methyldi(decyl)silane, ethyldi(octyl)silane, methyl(octyl)decylsilane, methyl(hexyl)decylsilane, tri(octyl)silane, tri(decyl)silane, tri(dodecyl)silane, and their mixtures.

The dialkylsilane and/or trialkylsilane is reacted with an alpha-olefin having from 2 to 20 carbon atoms, preferably from 8 to 20 carbon atoms; the alpha-olefin utilized may be a single form of alpha-olefin, such as, 1-octene or 1-decene, or may comprise a mixture of alpha-olefins, such as, for example, a mixture of 1-octene with 1-decene. If a mixture of alpha-olefins is utilized, the relative amounts of alpha-olefins may be varied as desired.

Suitable alpha-olefins include ethylene, propylene, 1-butene, 1-pentene, 1-hexene, 1-octene, 1-nonene, 1-decene, 1-dodecene, 1-tetradecene, and etc.

Any suitable combination of the aforesaid dialkylsilane and/or trialkylsilane with the 1-olefin may be utilized. For one particular application, at least one of the alkyl groups present on the silane represents an alkyl radical of from one to three carbon atoms while the other alkyl present in the alkylsilane, the same or different, represent at least one alkyl radical containing from 8 to 20 carbon atoms per molecule. The reason for this requirement is that a tetraalkylsilane carrying one short and three long alkyl groups will have pour points low enough to be fluid even at −65° F., as needed for operations in the Arctic region. When all four alkyl groups on the silicon are long, the product will have higher pour points, and therefore will be fluid only at higher temperatures such as around 0° F. or even higher.

The process of the present invention requires the use of an inert, halogen-free solvent. Any solvent can be used which is inert under reaction conditions. Suitable solvents include, for example, benzene, toluene, xylene, and n-octane, n-decane, or the like. Surprisingly, it has been found that the use of a saturated hydrocarbon solvent, such as saturated product in accordance with the present process, provides a higher percentage of saturated product, while the omission of a solvent or the use of unsaturated olefin as solvent results in a higher percentage of unsaturated product. Accordingly, the relative amounts of saturated and unsaturated silahydrocarbon product can be controlled by selecting the appropriate solvent or by omission of an extraneous solvent.

Any suitable rhodium-containing catalyst can be used in the present invention, such as, for example, chlorocarbonylbis(triphenylphosphine)rhodium(I), $RhCl(CO)(PPh_3)_2$; chlorotris(triphenylphosphine)rhodium(I), $RhCl(PPh_3)_3$; chlorotris(tri-p-tolylphosphine)rhodium(I), $RhCl[(CH_3C_6H_4)_3P]_3$; hydridocarbonyltris(triphenylphosphine)rhodium(I), $RhH(CO)(PPh_3)_3$. The rhodium can be deposited on a suitable support, such as, for example, from about 0.1 to about 10, preferably from about 0.5 or one to about 5 weight percent of the total catalyst as elemental rhodium. Suitable supports include charcoal, alumina, silica, zirconia or the like.

It was found that in the process of the present invention the hydrosilylation conditions have a direct effect upon the relative amounts of saturated and unsaturated silahydrocarbons produced. Suitable temperatures include about 30° to about 200° C., with about 50° to about 125° C. being preferred. However, the use of temperatures in the range from about 60° to about 125° C., preferably 65° to about 110° C. favor the production of saturated silahydrocarbons, while the use of temperatures from about 30° to about 60° C., preferably 40° to about 55° C. favor the production of unsaturated silahydrocarbons. Suitable pressures include from about one atmosphere to about 35 atmospheres, preferably from about one to about 10 atmospheres. The effect of temperature upon the ratio of saturated to unsaturated silahydrocarbons product is surprising in view of the fact that it had been thought that the relative yield of saturated silahydrocarbons and unsaturated silahydrocarbons remains substantially constant regardless of temperature. Thus, by selecting appropriate temperature conditions, the silahydrocarbon product can be "tailor-made" to provide the desired saturated to unsaturated silahydrocarbon ratio.

Suitable catalyst concentrations include from about $1 \times 10^{-5}$ to about $1 \times 10^{-2}$ millimoles of catalyst per millimole of dialkyl- and/or trialkylsilane, preferably from about $1 \times 10^{-4}$ to about $1 \times 10^{-3}$ millimoles of catalyst per millimole of silane. Likewise, it was found that the catalyst concentration has a direct effect upon the ratio of saturated to unsaturated silahydrocarbon produced. Thus, a catalyst concentration in the lower portion of the foregoing range favors the production of saturated silahydrocarbons, while a higher catalyst concentration favors unsaturated silahydrocarbons. Once again, this direct effect of catalyst concentration upon silahydrocarbon product is contrary to the prior belief that catalyst concentration has only a very minor affect.

The process of the present invention results in the production of unsaturated silahydrocarbons having the structural formula

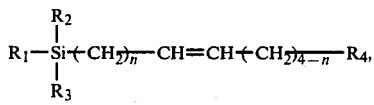

wherein $R_1$ represents an alkyl group having from one to about 20 carbon atoms per molecule, $R_2$ and $R_3$ each represent the same or different alkyl groups having from 6 to about 20 carbon atoms per molecule, $R_4$ represents an alkyl group having from one to about 8 carbon atoms per molecule, and n represents an integer from 0 to 4, inclusive with the proviso that the molecular weight of the unsaturated silane hydrocarbon is above 300.

Preferred unsaturated silahydrocarbons having the foregoing structural formula are those in which $R_1$ represents an alkyl group having from one to about 12 carbon atoms, most preferably one to about 3 carbon atoms per molecule, $R_2$ and $R_3$ each represent the same or different alkyl groups having from 7 to about 14 carbon atoms, most preferably from 8 to about 12 carbon atoms per molecule, $R_4$ represents an alkyl group from 2 to about 6 carbon atoms, most preferably from about 2 to about 4 carbon atoms per molecule, and n represents an integer of from 0 to about 3, most preferably 0 to 2.

Likewise, corresponding saturated silahydrocarbons are produced, having the structural formula

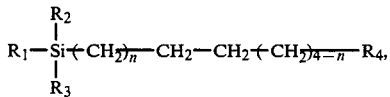

wherein $R_1$ represents an alkyl group having from one to about 20 carbon atoms per molecule, $R_2$ and $R_3$ each represent the same or different alkyl groups having from 6 to about 20 carbon atoms per molecule, $R_4$ represents an alkyl group having from one to about 8 carbon atoms per molecule, and n represents an integer from 0 to 4, inclusive.

Preferably, the saturated silahydrocarbons have the foregoing structural formula in which $R_1$ represents an alkyl group having from one to about 12 carbon atoms, most preferably one to about 3 carbon atoms per molecule, $R_2$ and $R_3$ each represent the same or different alkyl groups having from 7 to about 14 carbon atoms, most preferably from 8 to about 12 carbon atoms per molecule, $R_4$ represents an alkyl group from 2 to about 6 carbon atoms, most preferably from about 2 to about 4 carbon atoms per molecule, and n represents an integer of from 0 to about 3, most preferably 0 to 2.

Preferred saturated silahydrocarbons include methyl tri(octyl)silane, methyltri(decyl)silane, methyltri(dodecyl)silane, methyldi(octyl)decylsilane, methyldi(decyl)octylsilane, ethyltri(octyl)silane, methyltri(decyl)silane, tetra(octyl)silane, tetra(decyl)silane, hexyl(heptyl)(octyl)(nonyl)silane, methyl(octyl)(nonyl)(decyl)silane, tri(octyl)(tetradecyl)silane, etc., and mixtures, thereof.

The molecular weight of the product mixture of saturated and unsaturated silahydrocarbons should be above 300, preferably above 350, and most preferably above 375 in order to have the required viscosities, pour points, low volatilities, and high flash and/or fire points as required in a lubricant.

The unsaturated compounds of the present invention in descending order of preference are when n=0, i.e., compounds of type

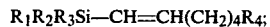

when n=1, i.e., compounds of type

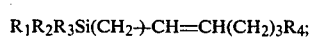

when n=2, i.e., compounds of type

when n=3, i.e., compounds of type

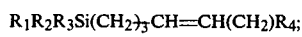

and when n=4, i.e., compounds of type

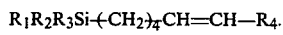

Each type of product can be present as the corresponding cis-isomer, trans-isomer, or a mixture of the cis- and trans-isomers. Most preferably, the product consists of a mixture of the above product types having n=0, 1, and 2, predominantly.

Likewise, unsaturated silahydrocarbons are produced, such as the cis and/or trans isomers: methyldi(octyl)silyl-1-octene, methyldi(octyl)silyl-2-octene, methyldi(decyl)silyl-1-decene, methyldi(decyl)silyl-2-decene, methyldi(dodecyl)silyl-1-dodecene, methyldi(dodecyl)silyl-2-dodecene, methyldi(octyl)silyl-1-decene, methyldi(octyl)silyl-2-decene, methyldi(decyl)silyl-1-octene, methyldi(decyl)silyl-2-octene, ethyldi(octyl)silyl-1-octene, ethyldi(octyl)silyl-2-octene, methyldi(decyl)silyl-1-decene, ethyldi(decyl)silyl-2-decene, tri(octyl)silyl-1-octene, tri(octyl)silyl-2-octene, tri(decyl)silyl-1-decene, tri(decyl)silyl-2-decene, hexyl(heptyl)(octyl)silyl-1-nonene, hexyl(heptyl)(pctyl)silyl-2-nonene, methyl(octyl)(nonyl)silyl-1-decene, methyl(octyl)(nonyl)silyl-2-decene, tri(octyl)silyl-1-tetradecene, tri(octyl)silyl-2-tetradecene, etc. and their mixtures.

Suitable weight ratios of olefin to dialkylsilane and/or trialkylsilane includes a weight ratio of from about 0.5 to about 20 to one, preferably from about one to about 10 to one. Higher ratios of olefin to alkylsilane are preferred for economic reasons, since olefinic hydrocarbons are less expensive, and are easier to recover and recycle.

When the silahydrocarbon product of the present invention is to be used as an additive for lubricating oils or hydraulic fluids, it is preferred that the product contain a major amount of saturated silahydrocarbon, e.g., at least 75 weight percent saturated silahydrocarbon, preferably about 85 percent or greater of the saturated silahydrocarbon product. The process of this invention can provide below about 25 weight percent unsaturated silahydrocarbon product, for example, from about 3 to about 25 weight percent unsaturated product, preferably from about 5 or 10 to about 20 weight percent.

The lubricating oil composition of the present invention can contain, in addition to the admixture of saturated and unsaturated silahydrocarbons, additives that have been conventionally employed with silahydrocarbons to impart storage stability, oxidative stability, lubricity, and other conventions to meet required specifications. Such additives include antiwear additives to enhance lubricity, such as tricresylphosphate, antioxidants, such as 2,6-di-t-butyl-p-cresol, as well as additives to impart corrosion stability, such as hindered phenolics. Likewise, additional additives may be employed, such as defoaming agents, emulsifying agents, metal passivators and other conventional additives commonly used with base oils.

The presence of unsaturation in the unsaturated silahydrocarbon further permits formation of fluids and lubricants with improved "built in" lubricating properties through the reaction of the unsaturated compounds of the present invention with dialkyldithiophosphoric acid or sulfur compounds.

The preferred dialkyldithiophosphoric acids have the formula

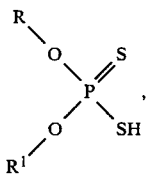

wherein R and R$^1$ each represent the same or different alkyl groups having from about 4 to 10 carbon atoms per molecule, preferably from about 6 to 8 carbon atoms per molecule, and can be linear, such as an n-hexyl group, cyclic such as, for example, cyclopentyl or cyclohexyl groups, or may be highly branched.

Suitable mercaptans include, for example, sulfur, $HSCH_2CH_2OH$, $HSCH_2CH_2SH$, $HSCH_2CH_2COOH$, $HSCH_2CH_2COOC_2H_5$, and the like.

Suitable reaction conditions for adding the sulfur or phosphorus compounds to the unsaturated compounds of the present invention include, for example, temperatures in the range of between about 30° to about 200° C., preferably from about 50° to about 175° C., under a pressure of from about one atmosphere to about 50 atmospheres, preferably from about one to about 5 atmospheres. Suitable reaction times include from about 0.5 to about 48 hours, preferably from about one to about 12 hours. To assist with the reaction, inert solvents such as toluene or xylenes or normal decane can be used advantageously to keep the reaction mixture in a homogeneous phase and thus improve the contact between the reactants.

The aforesaid sulfur and phosphorus compounds react with the unsaturated silahydrocarbons of the present invention to form compounds having the structural formula

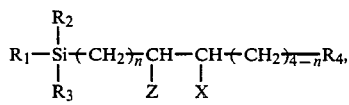

wherein R$_1$ represents an alkyl group having from one to about 20 carbon atoms per molecule, R$_2$ and R$_3$ each represent the same or different alkyl groups having from 6 to about 20 carbon atoms per molecule, R$_4$ represents an alkyl group having from one to about 8 carbon atoms per molecule, n represents an integer from 0 to 4, Z and X each represent a sulfur moiety or hydrogen with the proviso that only one of Z or X represents a sulfur moiety while the other represents hydrogen.

Preferred unsaturated silahydrocarbons having the foregoing structural formula are those in which R$_1$ represents an alkyl group having from one to about 12 carbon atoms, most preferably one to about 3 carbon atoms per molecule, R$_2$ and R$_3$ each represent the same or different alkyl groups having from 7 to about 14 carbon atoms, most preferably from 8 to about 12 carbon atoms per molecule, R$_4$ represents an alkyl group from 2 to about 6 carbon atoms, most preferably from about 2 to about 4 carbon atoms per molecule, and n represents an integer of from 0 to about 3, most preferably 0 to 2.

Preferred compounds having the structure include, for example,

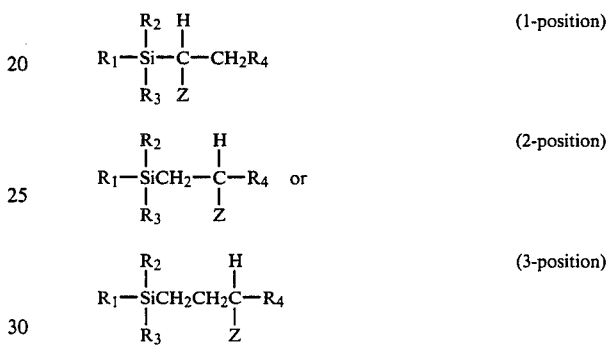

in which R$_1$, R$_2$, R$_3$ and R$_4$ are defined as before and Z represents a sulfur moiety resulting from the reaction of an unsaturated silahydrocarbon with a dialkyldithiophosphoric acid or a sulfur compound, as described above. As seen from the substituted structures, the sulfur moiety is preferably substituted at the 1-, 2- or 3-position relative to the silicon atom. When sulfur, per se or difuctional sulfur compounds, such as HSCH$_2$CH$_2$HS are used, crosslinking can occur resulting in compounds, for example, having the formula

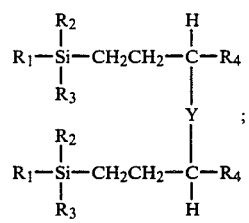

which is the result of crosslinking two 3-position isomers wherein R$_1$, R$_2$, R$_3$ and R$_4$ are defined as before and Y represents the sulfur moiety —S—, or —S(CH$_2$)$_2$S. Similar structures can result from crosslinking two of the 1-position isomers, two of the 2-position isomers, or a combination of 1-position with 2-position or 3-position isomers, or a combination of 2-position isomers with 3-position isomers or mixtures thereof.

The process of the present invention is illustrated by the following examples. The percentages are by weight unless otherwise indicated.

EXAMPLE 1

A mixture of 69 grams of methyldecylsilane and 200 grams of 1-octene was reacted in the presence of 0.0095 gram of chlorotris(triphenylphosphine)rhodium(I) at 80°–90° C., under a nitrogen atmosphere, while stirring for 2 hours. Analysis by GLC showed the product to contain 28 percent of unsaturated vinyl and allylsilanes [$CH_3Si(C_8H_{17}(C_{10}H_{21})CH=CHC_6H_{13}$ and $CH_3Si(C_8H_{17})(C_{10}H_{21})CH_2CH=CHC_5H_{11}$], and 72 percent of methyldioctyldecylsilane. The unreacted octenes were stripped off on a rotary evaporator and the residue was hydrogenated in a Parr shaker in toluene solvent until no further hydrogen uptake was evident. Hydrogenation was conducted using a rhodium chloride (triphenylphosphine) catalyst at a temperature of 75° C. under a hydrogen atmosphere of 2–3 atmospheres for 12 hours.

Distillation revealed an 85 percent yield of methyldioctyldecylsilane having a boiling point of 200° C. (0.55 mm). The viscosity in centistokes was: −65° F., 1944; −40° F., 529; 0° F., 102.6; 100° F., 9.5; and 210° F., 2.7. The product had a pour point of below −85° F.

EXAMPLE 2

A mixture of 61 grams of methyloctylsilane and 186 grams of 1-octene was reacted in the presence of 0.0075 gram of chlorotris(triphenylphosphine)rhodium(I) for 2.5 hours at 85°–89° C. Analysis by GLC showed a total of 15 percent of unsaturated product. After removing unreacted octene by stripping, the residue was hydrogenated as in Example 1. Distillation revealed an 86 percent yield of methyltri(octyl)silane having a boiling point of 188°–189° C. (0.9 mm).

EXAMPLE 3

A mixture of 75 grams of methyldecylsilane and 202 grams 1-decene was reacted in the presence of 0.0040 grams of chlorotris(triphenylphosphine)rhodium(I) at 87°–95° C. for one hour. The unreacted decene was stripped off under high vacuum and the residue hydrogenated as above. Distillation gave an 80 percent yield of methyltri(decyl)silane having a boiling point of 230°–233° C. (0.95 mm).

EXAMPLE 4

A mixture of 72.6 grams methyloctylsilane and 200 grams of 1-decene was reacted in the presence of 0.0042 gram of chlorotris(triphenylphosphine)rhodium(I) for one hour at 87°–100° C. After stripping off unreacted decene under high vacuum, followed by hydrogenation of the residue, and distillation, resulted in an 86 percent yield of methyldidecyloctylsilane having a boiling point of 200°–206° C. (0.25 mm).

EXAMPLE 5

A mixture of 40.5 grams methyloctylsilane, 22 grams of methyldecylsilane, 130 grams of 1-octene and 70 grams of 1-decene was reacted in the presence of 0.0032 gram of chlorotris(triphenylphosphine)rhodium(I) for two hours at 92°–111° C. On work-up, followed by hydrogenation and distillation, a 79 percent yield of mixed silanes was formed having a boiling point of 175° (0.8 mm)–215° C. (0.5 mm). An analysis of the silane product is presented in Table I below:

TABLE I

| Product Isomer Composition | % GLC Total | Distilled |
|---|---|---|
| Methyltrioctylsilane | 26.3 | 28.8 |
| Methyldioctyldecylsilane | 42.7 | 49.7 |
| Methyloctyldidecylsilane | 25.7 | 18.3 |

TABLE I-continued

| Product Isomer Composition | % GLC Total | Distilled |
|---|---|---|
| Methyltridecylsilane | 4.3 | 3.2 |

EXAMPLES 6–9

The following examples were conducted in order to determine the effect of temperature upon the course of the hydrosilylation reaction. Triethylsilane was reacted with various 1-alkenes in the presence of chlorotris(triphenylphosphine)rhodium(I) and olefin to silane molar ratio of 6.5/1.0 under the conditions shown in Table II, below:

TABLE II

| Example No. | Olefin | Catalyst Concentration | Temp. (°C.) | Silane Conversion (%) | Wt. Percent Unsaturated Product |
|---|---|---|---|---|---|
| 6 | 1-hexene | $1.2 \times 10^{-3}$ | 64–65 | 99 | 69 |
| 7 | 1-heptene | $1.1 \times 10^{-3}$ | 94–95 | 97 | 25 |
| 8 | 1-octene | $9.7 \times 10^{-4}$ | 61–62 | 75 | 40 |
| 9 | 1-octene | $9.7 \times 10^{-4}$ | 99–100 | 91 | 21 |

As seen in Table II, at a comparable catalyst level, lower temperature increases the amount of unsaturated product, while a higher temperature gives a smaller amount of unsaturated product. Thus, the foregoing examples demonstrate that in the process of the present invention, the reaction is temperature dependent, and the saturate-unsaturate product mix can be controlled by temperature.

EXAMPLES 10–13

The following examples were conducted to determine the effect of catalyst concentration, per se upon the hydrosilylation reaction. The tests were made at temperatures of 80°–89° C. using methyloctylsilane and 1-octene as the reactants at an olefin to silane molar ratio of 4.1 to one. The results are set forth in Table III, below:

TABLE III

| Example No. | Catalyst Concentration | Relative Catalyst Amount | Conversion (%) | Temp. (°C.) | Wt. Percent Unsaturated Product |
|---|---|---|---|---|---|
| 10 | $1.8 \times 10^{-4}$ | 20 | 100 | 80–83 | 20.0 |
| 11 | $3.6 \times 10^{-5}$ | 4 | 100 | 80–84 | 10.7 |
| 12 | $0.9 \times 10^{-5}$ | 1 | 100 | 81–86 | 3.7 |
| 13 | $4.0 \times 10^{-6}$ | 0.4 | — | 83–89 | — |

As seen in Table III, the greater the catalyst concentration, the higher the yield of unsaturates.

EXAMPLES 14–18

In order to determine the effect of solvents on the hydrosilylation reaction, triethylsilane was reacted with 1-hexene using the same catalyst under the conditions shown in Table IV, below:

TABLE IV

| Example No. | Catalyst Concentration | Solvent | Olefin to Silane Ratio (mol/mol) | Temp. (°C.) | Silane Conversion (%) | Wt. Percent Unsaturated Product |
|---|---|---|---|---|---|---|
| 14 | $1 \times 10^{-4}$ | toluene | 2.1/1 | 85–90 | 55 | 8 |

TABLE IV-continued

| Example No. | Catalyst Concentration | Solvent | Olefin to Silane Ratio (mol/mol) | Temp. (°C.) | Silane Conversion (%) | Wt. Percent Unsaturated Product |
|---|---|---|---|---|---|---|
| 15 | $8.6 \times 10^{-4}$ | toluene | 2.1/1 | 80–85 | 70 | 23 |
| 16 | $8.8 \times 10^{-4}$ | decane | 2.1/1 | 84–89 | 74 | 23 |
| 17 | $8.6 \times 10^{-4}$ | none | 11.5/1 | 88–95 | 94 | 62 |
| 18 | $6.7 \times 10^{-5}$ | none | 11.5/1 | 86–90 | 95 | 47 |

As seen in Table IV, Examples 14 and 15 demonstrate that the higher catalyst concentration produces more unsaturated product under otherwise identical conditions. Comparing Examples 15 and 16 it is seen that the use of toluene or decane has a roughly similar effect. Comparing Examples 16 and 17, it is seen that without the use of solvent, i.e., wherein excess olefin is used as solvent, a higher percentage of unsaturated product is produced. Comparing Examples 17 and 18, it is seen using a lower catalyst concentration results in less unsaturated product under otherwise similar conditions.

EXAMPLE 19

A mixture of 27 grams of methyloctylsilane and 100 grams of 1-octene was reacted in the presence of 0.010 gram of chlorotris(triphenylphosphine)rhodium(I) by stirring under nitrogen for 1.25 hours at 92°–105° C. The distillation produced one major fraction having a boiling point of 185°–190° C. (0.9 mm), whose composition was as follows:

|  | Wt. % |
|---|---|
| Methyltrioctylsilane | 76 |
| Methyldi(octyl)silyl-1-octene | 14 |
| Methyldi(octyl)silyl-2-octene | 10 |

EXAMPLE 20

A mixture of 1.53 grams of methyldidecylsilane, and 0.70 gram of 1-decene in 5 milliliters of benzene was reacted for 25 hours at 50° C. in the presence of 0.005 gram hydridocarbonyltris(triphenylphosphine)rhodium(I). Chromatographic analysis showed that an 85 percent yield of methyltridecylsilane was formed at a 65 percent silane conversion.

EXAMPLE 21

The test of Example 20 was repeated using 0.005 gram of chlorotris(triphenylphosphine)rhodium(I). The reaction was over in one hour at 50° C., and produced an 85 percent yield of methyltridecylsilane and 15 percent of methyldidecylsilyl-1-decene and methyldidecylsilyl-2-decene.

EXAMPLE 22

A mixture of 2.0 grams trioctylsilane and 10 grams 1-octene in 5 milliliters of toluene was reacted for 2 hours at 75°–80° C. in the presence of 0.009 gram of chlorotris(triphenylphosphine)rhodium(I) to yield 80 weight percent tetraoctylsilane.

EXAMPLE 23

A mixture of 1.3 grams of hexylsilane, 10 grams of 1-octene and 0.02 gram of hydridocarbonyltris(triphenylphosphine)rhodium(I) were reacted in 5 milliliters of toluene at 100° C. for 1.3 hour. Analysis by GLC showed practically no reaction.

EXAMPLE 24

The procedure of Example 23 was repeated using 0.23 gram of chlorotris(triphenylphosphine)rhodium(I), but no solvent. After 2 hours at 100° C., most of the silane remained unreacted.

EXAMPLE 25

A mixture of triethylsilane (0.5 g) and 1-tetradecene (1.0 g) in toluene (5 ml) was reacted in the presence of 0.15 gram of 5 percent chlorotris(triphenylphosphine)rhodium(I) at 90° C. for 6 hours. Analysis by GLC of the product showed that triethyltetradecylsilane was formed (77%), along with triethylsilyl-1-tetradecene and triethylsilyl-2-tetradecene (23%).

EXAMPLE 26

A mixture of silahydrocarbons was formulated containing saturated compounds of the type $CH_3Si(C_8H_{17})_{3-x}(C_{10}H_{21})_x$ (88%) [x=0, 46%; x=1, 33%; x=2, 13%; and x=3, 8%], and unsaturated compounds of the type $CH_3Si(C_8H_{17})_{2-x}(C_{10}H_{21})_x(CH=CHC_8H_{17})_n(CH=CHC_6H_{13})_{1-n}$ (6%)

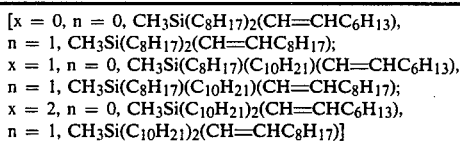

and type $CH_3Si(C_8H_{17})_{2-x}(C_{10}H_{21})_x(CH_2CH=CHC_7H_{15})_n(CH_2CH=CHC_5H_{11})_{1-n}$ (6%)

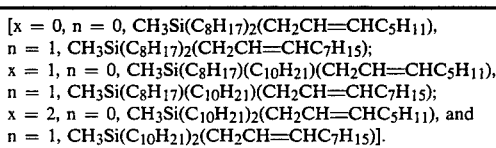

The mixture was subjected to thermal stability test for 6 hours at 371° C. under nitrogen, whereupon a 100° F. viscosity loss of 11.2 percent was obtained. The mixture was thereafter formulated with tricresylphosphate (A), a lubricity agent commonly used with hydrocarbon based hydraulic oils and 2,6-di-tert-butyl-p-cresol (B) as an antioxidant. The results of the conventional four-ball test using a 40 kilogram load, a temperature of 75° C., 600 RPM for a period of one hour resulting in the results shown below:

TABLE V

| Additive | Conc., wt. % | Wear Scar (mm) |
|---|---|---|
| Base oil alone | — | 1.0 |
| Additive A + Additive B | 3.0 1.0 | 0.67 |
| Additive A + Additive B | 5.0 1.0 | 0.55 |

The above clearly show that silahydrocarbon mixtures of the present invention are effective hydraulic oil fluids.

EXAMPLE 27

A conventional lubricant formulation utilizing synthetic hydrocarbons and commercially available additives is tested in which a portion of the synthetic hydrocarbon is replaced by the silahydrocarbon mixture of the present invention.

The synthetic oil contains a light component (I) having an average molecular weight and an average carbon number of 30 with the following viscosity:

TABLE VI

| Viscosity | Cs. |
| --- | --- |
| −65° F. | 10980 |
| −40° F. | 2040 |
| 0° F. | 280 |
| 100° F. | 16 |
| 210° F. | 3.65 |

The oil contains a heavier synthetic hydrocarbon component (II) having an average molecular weight of 565 and an average carbon number of 40 with the following viscosity:

TABLE VII

| Viscosity | Cs. |
| --- | --- |
| −65° F. | 62000 |
| −40° F. | 8200 |
| 0° F. | 877 |
| 100° F. | 34 |
| 210° F. | 6 |

The oil contains 20 weight percent of the lighter synthetic hydrocarbon (I), 60 weight percent of the heavier synthetic hydrocarbon (II), 6 weight percent of a commercial viscosity index improver and pour point depressant, and 14 weight percent of an admixture containing antioxidant, antiwear and antirust agents.

The resulting lubricating oil has the following specifications:

TABLE VIII

| Viscosity, Cs. | | Accepted Range |
| --- | --- | --- |
| −13° F. | 4200 | 6700 (max) |
| 0° F. | 2100 | — |
| 100° F. | 66 | 55–75 |
| 210° F. | 11 | 10–11 |

A silahydrocarbon mixture in accordance with the present invention having the formula

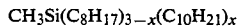

$CH_3Si(C_8H_{17})_{3-x}(C_{10}H_{21})_x$

[x=0, 48%; x=1, 34%; x=2, 15%; and x=3, 3%] has an average molecular weight of 410 and an average carbon number of 29 with the following viscosity:

TABLE IX

| Viscosity | Cs. |
| --- | --- |
| −65° F. | 1800 |
| −40° F. | 470 |
| 0° F. | 94 |
| 100° F. | 9 |
| 210° F. | 3 |

The aforesaid lubricating oil composition was tested against the identical composition with the exception that the synthetic hydrocarbon (I) is replaced by the silahydrocarbon mixture for comparative purposes in the amount of 20 weight percent.

The synthetic hydrocarbon was compared with the lubricating oil containing the silahydrocarbon mixture in a thermal stability test in which the viscosity of each test sample was measured before and after the thermal stability test in which the composition was subjected to a temperature of 371° C. for 6 hours under nitrogen. The results are set forth below in Table X:

TABLE X

| Fluid | % Viscosity Loss (100° F.) |
| --- | --- |
| Synthetic Hydrocarbon 1 | 55 |
| Silahydrocarbon Mixture | 11 |
| 50:50 Mixture of above fluids | 25 |

The results set forth in Table X demonstrate that the use of a silahydrocarbon mixture provides a much smaller loss in viscosity as compared with the conventional lubricating oil containing synthetic hydrocarbon (I) and provides far superior thermal stability.

The lubricating oil composition containing the novel silahydrocarbon mixture has excellent viscosity properties as follows:

TABLE XI

| Viscosity | cSt. |
| --- | --- |
| 100° F. | 59.6 |
| 210° F. | 10.4 |

EXAMPLE 28

Sulfurization of the unsaturated silahydrocarbon of the present invention can be carried out in a manner similar to that reported by Bacha and Hill in U.S. Pat. No. 4,218,331, 1980, for the sulfurization of dioleyl adipate. Twenty-five grams of a silahydrocarbon mixture, $CH_3Si(C_8H_{17})_{3-x}(C_{10}H_{21})_x$, x=0, 46%; x=1, 33%; x=2, 13%, x=3, 3%, containing 12 percent unsaturated silahydrocarbon are charged to a flask equipped with a stirrer, thermometer, reflux condenser and heating mantle. The temperature is raised to 130° C. and 0.25 gram of elemental sulfur is added. The temperature is then raised to 180° C. and held while the mixture is sparged with nitrogen until hydrogen sulfide is no longer expelled. Upon cooling, the sulfurized silahydrocarbon is obtained.

EXAMPLE 29

The reaction of dialkyldithiophosphoric acids with unsaturated silahydrocarbons is accomplished by a procedure similar to that described in British Pat. No. 1,347,845. Ten grams of the silahydrocarbon mixture used in Example 2 and 1.05 grams dioctyldithiophosphoric acid are refluxed in 100 milliliters of toluene for 3 hours. The solvent is stripped in vacuo to yield substituted product.

What is claimed is:

1. A process for the production of a mixture of saturated and unsaturated silahydrocarbons which comprises contacting an admixture comprising
   (A) at least one alpha-olefin containing from 2 to about 20 carbon atoms per molecule, and
   (B) at least one alkylsilane selected from the group consisting of (i) a dialkylsilane having the formula R—SiH$_2$—R$_1$ (ii) a trialkylsilane having the formula R—SiH(—R$_1$)$_2$ and (iii) mixtures thereof, wherein R and R$_1$, the same or different, each represent an alkyl radical of from one to 20 carbon atoms per molecule, with a catalyst comprising a homogeneous, monomeric rhodium-containing catalyst having a basicity substantially equal to or less than that provided by a rhodium-containing catalyst having a triphenyl phosphine ligand or a heterogeneous rhodium-containing catalyst in a halogen-free inert solvent, said process conducted at a temperature of from about 30° to about 200° C., a weight ratio of olefin to alkylsilane of from about 0.5 to about 20 to one and a catalyst concentration of from about $1\times10^{-5}$ to about $1\times10^{-2}$ millimoles of catalyst per millimole alkylsilane, to produce a mixture containing saturated silane hydrocarbons and an unsaturated silahydrocarbon having the formula

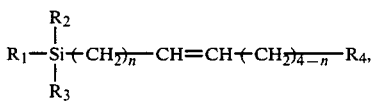

wherein R$_1$ represents an alkyl group having from one to about 20 carbon atoms per molecule, R$_2$ and R$_3$ each represent the same or different alkyl groups having from 6 to about 20 carbon atoms per molecule, R$_4$ represents an alkyl group having from one to about 8 carbon atoms per molecule, and n represents an integer from 0 to 4, inclusive with the proviso that the molecular weight of the unsaturated silane hydrocarbon is above 300.

2. The process of claim 1 wherein the process is conducted in a temperature range of from about 50° to 125° C.

3. The process of claim 1 wherein the catalyst concentration is from about $1\times10^{-4}$ to about $1\times10^{-3}$ millimoles of catalyst per millimole alkylsilane.

4. The process of claim 1 wherein the ratio of said alpha-olefin to said alkylsilane is from about one to about 10 to one.

5. The process of claim 1 wherein said alkylsilane is a dialkylsilane having the formula R—SiH$_2$—R$_1$ wherein R and R$_1$, the same or different, each represent methyl, hexyl, octyl, and decyl groups.

6. The process of claim 1 wherein said catalyst is chlorotris(triphenylphosphine)rhodium(I).

7. The process of claim 1 wherein said halogen-free solvent is the reactant olefin.

8. The process of claim 1 wherein said mixture of saturated and unsaturated silahydrocarbons consist essentially of at least 75 weight percent of saturated silahydrocarbons.

9. An unsaturated silahydrocarbon having the formula

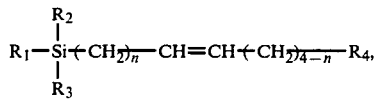

wherein R$_1$ represents an alkyl group having from one to about 20 carbon atoms per molecule, R$_2$ and R$_3$ each represent the same or different alkyl groups having from 6 to about 20 carbon atoms per molecule, R$_4$ represents an alkyl group having from one to about 8 carbon atoms per molecule, and n represents an integer from 0 to 4, inclusive with the proviso that the molecular weight of the unsaturated silane hydrocarbon is above 300.

10. The silahydrocarbon of claim 9 wherein R$_1$ represents an alkyl group having from one to about 12 carbon atoms, R$_2$ and R$_3$ each represent the same or different alkyl groups having from 7 to about 14 carbon atoms, and R$_4$ represents an alkyl group of from 2 to about 6 carbon atoms.

11. The silahydrocarbon of claim 9 wherein n represents an integer of from 0 to 3.

12. The silahydrocarbon of claim 11 wherein n represents an integer of from 0 to 2.

13. The silahydrocarbon of claim 9 selected from the group consisting of

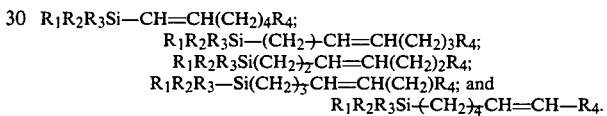

14. A lubricating composition comprising (A) a minor amount of unsaturated silahydrocarbon having the formula

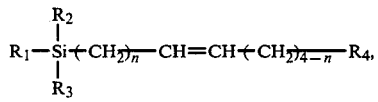

wherein R$_1$ represents an alkyl group having from one to about 20 carbon atoms per molecule, R$_2$ and R$_3$ each represent the same or different alkyl groups having from 6 to about 20 carbon atoms per molecule, R$_4$ represents an alkyl group having from one to about 8 carbon atoms per molecule, and n represents an integer from 0 to 4, inclusive with the proviso that the molecular weight of the unsaturated silane hydrocarbon is above 300, and (B) a major amount of saturated hydrocarbon, saturated silahydrocarbon or mixtures thereof.

15. The lubricating composition of claim 14 wherein said composition comprises a major amount of saturated hydrocarbons.

16. The lubricating composition of claim 14 wherein said composition contains a major amount of saturated silahydrocarbons.

17. The lubricating composition of claim 14 wherein said unsaturated silahydrocarbon is present in an amount of below about 25 weight percent.

18. The lubricating composition of claim 14 wherein said unsaturated silahydrocarbon is present in an amount of from about 5 to about 20 weight percent.

19. The lubricating composition of claim 14 wherein n represents an integer of from 0 to 2.

20. The lubricating composition of claim 14 wherein $R_1$ represents an alkyl group having from one to 3 carbon atoms per molecule, $R_2$ and $R_3$ each represent the same or different alkyl groups of from 8 to 12 carbon atoms per molecule, and $R_4$ represents an alkyl group of from 2 to 4 carbon atoms per molecule.

21. A lubricating composition additive having the formula

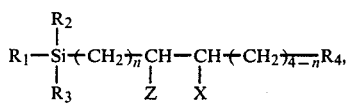

wherein $R_1$ represents an alkyl group having from one to about 20 carbon atoms per molecule, $R_2$ and $R_3$ each represent the same or different alkyl groups having from 6 to about 20 carbon atoms per molecule, $R_4$ represents an alkyl group having from one to about 8 carbon atoms per molecule, n represents an integer from 0 to 4, Z and X each represent a sulfur moiety or hydrogen with the proviso that only one of Z or X represents a sulfur moiety while the other represents hydrogen.

22. The lubricating composition of claim 21 wherein Z represents sulfur and X represents hydrogen.

23. The lubricating composition of claim 21 wherein X represents sulfur and Z represents hydrogen.

24. The process of claim 1, wherein said catalyst is a member selected from the group consisting of chlorocarbonylbis(triphenylphosphine)rhodium(I), $RhCl(CO)(PPh_3)_2$; chlorotris(triphenylphosphine)rhodium(I), $RhCl(PPh_3)_3$; chlorotris(tri-p-tolylphosphine)rhodium(I), $RhCl[(CH_3C_6H_4)_3P]_3$; hydridocarbonyltris(triphenylphosphine)rhodium(I), and $RhH(CO)(PPh_3)_3$.

* * * * *